Feb. 25, 1941. W. E. LAMMERTS Plant Pat. 455
ROSE PLANT
Filed Oct. 14. 1940
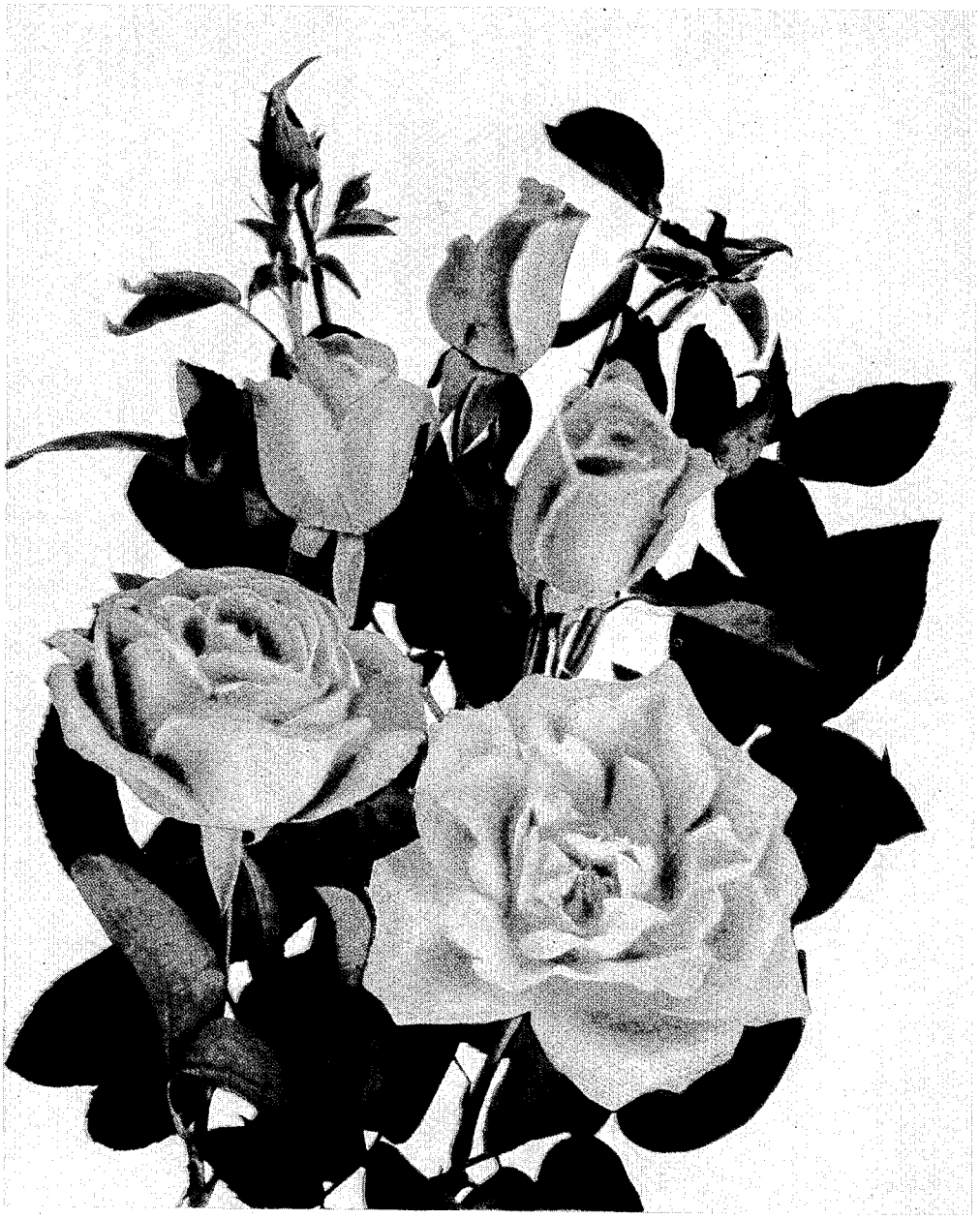
Inventor
W. E. Lammerts
By Robert Cobb
Attorneys Patented Feb. 25, 1941

Plant Pat. 455

UNITED STATES PATENT OFFICE

455

ROSE PLANT

Walter E. Lammerts, Ontario, Calif., assignor to Armstrong Nurseries, Ontario, Calif., a corporation of California Application October 14, 1940, Serial No. 361,191

1 Claim. (Cl. 47—61)

The present invention relates to a new and distinct variety of hybrid tea rose plant, the result of a definite effort to produce a rose of distinctiveness and having, as far as possible, the desirable characteristics of its parents.

The new variety originated as a seedling resulting from a cross of "Sister Therese" and "Crimson Glory," the objective referred to being attained in that it incorporates most of the good features of both of these plants with few, if any, of their shortcomings. It may be said generally speaking, that the habit of growth of the new rose more nearly resembles that of Crimson Glory, although more vigorous, while the mildew resistance and the shape of the bud more nearly approach that of Sister Therese.

More specifically, this rose is characterized as to novelty by the following distinguishing features:

The vigorousness of the plant which is comparable to the well known variety Radiance; the large, luxuriant foliage which possesses a high degree of mildew resistance; the free-branching habit of the plant which has the general habit of growing upright; the somewhat more than average amount of prickles both large and small; the long stems which are sufficiently strong to support the flower without bending the peduncle; the extremely long, streamlined bud, slightly flaring at the tip, spectrum red in color with occasional carmine markings on the outside of the bud, which opens to a flower of spectrum red, changing slightly to rose-red after the flower has been opened one day. The open flowers vary in size from four inches to as much as six inches in width and have a distinctive shape in the open flower in that the inner petals have a peculiar arching tendency with the lower portion of the petal in a vertical position and the upper portion of the petal in a horizontal position pointing outward. This tendency creates somewhat of an illusion as regards the petalage of the flower, for although the flowers have only from 25 to 35 petals, the effect given by these inner arching petals is of a flower of considerably more petalage since the stamens in the center do not become apparent until the flower is quite old.

Other characteristics include long clasping sepals which remain clasping the bud longer than is found in most roses; the extreme floriferousness of the plant; the substantial texture of the petals and their tendency to drop off cleanly when the flower is past the decorative stage; the only moderate fragrance of the flower which is usually produced on an individual stem, although occasionally on heavy canes originating near the base of the plant the flower will be produced in a cluster of several to a stem.

The following is a detailed description of this new rose, the color terminology employed therein being in accord with Ridgway's Color Standard.

Type: Tender; tall; bush; outdoor; seedling; for cut flowers and garden decoration.

Class: Hybrid tea.

Parentage:

*Seed parent.*—Soeur Therese.

*Pollen parent.*—Crimson Glory.

Propagation: It holds its distinguishing characteristics through succeeding propagations by grafting and budding.

*Flower*

Locality where grown: Ontario, California, near Dessau and San Antonio.

Flowers borne: Singly, sometimes three or more to stem; on normal, medium long stems.

Quantity of bloom: Abundant, outdoors.

Continuity: Continuous during growing season.

Fragrance: Slight; tea.

Bud:

*Peduncle.*—Long; slender; erect; numerous gland-tipped cilia and small prickles; from Deep Dull Yellow-Green, Plate XXXII, to near Rinnemann's Green, Plate XVIII, toward top.

*Before calyx breaks.*— *Size* — medium. *Form*—pointed with foliaceous appendages; glabrous on the surface of the bud; with slender, much cut foliaceous parts extending beyond the tip of the bud equal to three-fourths or more of its length on well grown plants.

*As calyx breaks.*—*Color*—Carmine, Plate I, to Spectrum Red, Plate I. Inner surface with fine tomentum; margins exposed before calyx breaks, lined with gland-tipped cilia. Margins unexposed lined with whitish tomentum.

*As first petal opens.*—*Size*—large. *Form*—very long pointed. *Color:* outside—Spectrum Red, Plate I, to Rose Red, Plate XII; inside—Carmine, Plate I, to Spectrum Red, Plate I. *Opening*—Opens up well.

Bloom:

*Size, when fully open.*—Very large, four inches to six inches.

*Petalage.*—Double, from 25 to 35 petals arranged regularly.

*Form.*—Very high center at first; becoming high centered; petals at first very tightly rolled outward; becoming later, at maturity, very loosely rolled outward.

Petals: Leathery, with inside satiny and outside somewhat shiny.

*Shape.*—Outside—obovate to suborbicular. Intermediate—obovate. Inside—Obovate-cuneate, with three notches usually.

*Color.*—May be modified by being margined with Thulite Pink, Plate XXVI.

This description of a newly opened flower was made from a rose grown outdoors, in August, 1940, at Ontario, California:

*Color.*—Outside petal: outside surface—between Spectrum Red, Plate I, and Rose Red, Plate XIII, Light Greenish Yellow, Plate V, at base; inside surface—Carmine, Plate I, to Spectrum Red, Plate I, to Lemon Chrome, Plate IV. Intermediate petal: outside surface—Spectrum Red, Plate I, to Light Greenish Yellow, Plate V; inside surface—Spectrum Red, Plate I, to Lemon Chrome, Plate IV. Inner petal: outside surface—Spectrum Red, Plate I, to Lemon Chrome, Plate IV; inside surface—Spectrum Red, Plate I, to Lemon Chrome, Plate IV.

This description was made from a rose that was open for three days outdoors, in August, 1940, at Ontario, California:

*Color.*—Outside petal: outside surface—near Begonia Rose, Plate I; Lemon Chrome at base, Plate IV; inside surface—near Rose Red, Plate XII. Inside petal: outside surface—near Begonia Rose, Plate I; Light Greenish Yellow at base, Plate V; inside surface—near Rose Red, Plate XII.

*General color effect.*—Newly opened flower—Spectrum Red, Plate I. Three days open—Rose Red, Plate XII.

*Behavior.*—Drop off cleanly; affected by cold, wet weather, fading from near Pale Rose Purple, Plate XXVI, to near Light Mallow Purple, Plate XII, and to Green Yellow, Plate V, to Light Green Yellow, Plate V, at base.

*Flower longevity.*—On bush in garden three days in August; cut roses grown outdoors kept at living-room temperatures four days in August. Not grown in greenhouse.

*Reproductive organs*

Stamens: Medium many; arranged regularly about pistils, mixed with petaloids.

Filaments: Medium long; Deep Chrome, Plate III, at base to Lemon Chrome, Plate IV, at tip; some near Rose Red, Plate XII; most with anthers.

Anthers: Medium large; color near Cadmium Yellow, Plate III; all open at once approximately.

Pollen: Moderate to abundant; near Cadmium Yellow, Plate III.

Pistils: Medium quantity.

Styles: Very uneven; medium long; thin; loosely separated; near Spectrum Red, Plate I, at tip; near Pale Viridine Yellow, Plate V, at base.

Stigma: Near Capucine Buff, Plate III.

Ovaries: Some protruding from calyx.

Hips: Globular to pear-shaped: very smooth while immature; walls thick, fleshy; rough when mature.

*Color.*—When half mature near Lime Green, Plate XXXI, on sunny side to near Absinthe Green, Plate XXXI, on other side with occasional spots and lines of corky growth.

Sepals: Permanent; very long; straight; spear-shaped.

*Color.*—Inside—base near Light Fluorite Green, Plate XXXII, to near tip near Malachite Green, Plate XXXII, foliaceous tip near Dark Dull Yellow Green, Plate XXXII, when old shaded Vinaceous Lilac, Plate XLIV, near base. Outside—near Turtle Green, Plate XXXII, at base to near Chromium Green, Plate XXXII, toward tip.

Seeds: Many; medium size.

*Plant*

Foliage:

*Leaves.*—Compound of three, five and sometimes seven leaflets; moderately abundant; moderately large; moderately heavy, leathery.

*Leaflets.*—Ovate to ovate-cuspidate, with apex acute, base round; margin simply serrate; serrations reduced at base to stipitate glands.

*Color.*—*Mature*—upper surface—near Dark Dull Yellow Green, Plate XXXII. Under surface—near Pois Green, Plate XLI. *Young*—upper surface—near Dark Anthracene Violet, Plate XXV. Under surface—Dark Indian Red, Plate XXVII.

*Rachis* (the supporting stem of the compound leaf).—Light to medium. Upper side—grooved, glandular. Under side—sparsely prickly; few gland-tipped celia.

*Stipules.*—Medium long; medium wide, with medium long points, turning out at an angle of usually more than 45°, slightly recurved toward the stem.

*Disease.*—Resistant to mildew.

Growth:

*Habit.*—Dwarf, bushy, upright, much branched.

*Growth.*—Vigorous.

*Canes.*—Moderately heavy.

*Main stems.*—*Color*—near Rinnemann's Green, Plate XVIII, with cracks in bark forming corky linear dots and lines of near Cinnamon, Plate XXIX, to Pecan Brown, Plate XXVIII, and shading near Dark Lavender, Plate XLIV, to near Anthracene Violet, Plate XLIV, on sides exposed to sun. *Large prickles*—several; medium long, slightly hooked downward, with medium long broad base. *Color*—near Russet, Plate XV. *Small prickles*—several. *Hairs*—few; elliptic to nearly round base; near Russet, Plate XV.

*Branches.*—Near Rinnemann's Green, Plate XVIII. *Large prickles*—several; medium long; nearly straight, slightly hooked downward, with short broad base; near Vinaceous Drab, Plate XLV, in color. *Small prickles*—several; near Vinaceous Drab, Plate XLV, in color. *Hairs*—few; near Vinaceous Drab, Plate XLV, in color.

*New shoots.*—Near Scheele's Green were not exposed to sun to near Dark Vinaceous Brown, Plate XXXIX. *Large prickles*—several; medium long; nearly straight, with short narrow base. *Color*—near Pansy Purple, Plate XII, at base to near Grape Green, Plate XLI, at tip. *Small prickles*—several; color near Pansy Purple, Plate XII, at base to near Grape Green, Plate XLI, at tip. *Hairs*—few; color near Pansy Purple, Plate XII, at base to near Grape Green, Plate XLI, at tip.

I claim:

A new and distinct variety of Hybrid Tea rose plant characterized as to novelty by its vigorousness, large and luxuriant foliage, free branching habit and upright growth, long and strong stems, attractive color, form, size, and arrangement of its blossoms, texture of the petals, long clasping sepals, extreme floriferousness of the plant, and delicate fragrance of the flower, substantially as shown and described.

WALTER E. LAMMERTS.